United States Patent
Kuntz et al.

(10) Patent No.: US 10,040,782 B2
(45) Date of Patent: Aug. 7, 2018

(54) HYDROCHLORIDE SALT FORM FOR EZH2 INHIBITION

(71) Applicants: Epizyme, Inc., Cambridge, MA (US); Eisai R&D Management Co., Ltd., Tokyo (JP)

(72) Inventors: Kevin W. Kuntz, Woburn, MA (US); Hyeong-wook Choi, Andover, MA (US); Steven Mathieu, Andover, MA (US); Kristen Sanders, Gilmanton, NH (US); Arani Chanda, Malden, MA (US)

(73) Assignees: Epizyme, Inc., Cambridge, MA (US); Eisai R&D Management Co., Ltd., Bunkyo-ku, Tokyo (JP)

( * ) Notice: Subject to any disclaimer, the term of this patent is extended or adjusted under 35 U.S.C. 154(b) by 0 days.

(21) Appl. No.: 15/029,848

(22) PCT Filed: Oct. 15, 2014

(86) PCT No.: PCT/US2014/060724
§ 371 (c)(1),
(2) Date: Apr. 15, 2016

(87) PCT Pub. No.: WO2015/057859
PCT Pub. Date: Apr. 23, 2015

(65) Prior Publication Data
US 2016/0237068 A1 Aug. 18, 2016

Related U.S. Application Data

(60) Provisional application No. 61/891,786, filed on Oct. 16, 2013.

(51) Int. Cl.
*C07D 405/12* (2006.01)
*A61K 31/5377* (2006.01)
*C07D 413/12* (2006.01)

(52) U.S. Cl.
CPC ........ *C07D 405/12* (2013.01); *A61K 31/5377* (2013.01); *C07D 413/12* (2013.01); *C07B 2200/13* (2013.01)

(58) Field of Classification Search
CPC .............. A61K 31/5377; C07D 405/12; C07D 413/12; C07B 2200/13
See application file for complete search history.

(56) References Cited

U.S. PATENT DOCUMENTS

| 5,716,993 A | 2/1998 | Ozaki et al. |
| 5,948,803 A | 9/1999 | Maeda et al. |

(Continued)

FOREIGN PATENT DOCUMENTS

| EP | 1357111 | 10/2003 |
| JP | 7033729 | 2/1995 |

(Continued)

OTHER PUBLICATIONS

Braña et al. "Reaction of N-(2-Pyridylmethyl)-3,5-dimethylbenzamide and N-(3-Pyridylmethyl)-3,5-dimethylbenzamide N-Oxides With Acetic Anhydride." Journal of Heterocyclic Chemistry, 19:6(1982),1297-1300.

(Continued)

*Primary Examiner* — Angela C Brown-Pettigrew
(74) *Attorney, Agent, or Firm* — Cooley LLP; Heidi A. Erlacher; Christine C. Pemberton

(57) ABSTRACT

Provided herein are novel solid forms of N-((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide hydrochloride, and related compositions and methods.

14 Claims, 4 Drawing Sheets

(56) References Cited

U.S. PATENT DOCUMENTS

| | | |
|---|---|---|
| 7,122,547 B1 | 10/2006 | Huth et al. |
| 7,252,968 B2 | 8/2007 | Jenuwein et al. |
| 7,442,685 B2 | 10/2008 | Zhang et al. |
| 7,563,589 B2 | 7/2009 | Zhang et al. |
| 7,923,219 B2 | 4/2011 | Wang et al. |
| 8,410,088 B2 | 4/2013 | Kuntz et al. |
| 8,765,732 B2 | 7/2014 | Kuntz et al. |
| 9,090,562 B2 | 7/2015 | Kuntz et al. |
| 9,175,331 B2 | 11/2015 | Kuntz et al. |
| 9,334,527 B2 | 5/2016 | Kuntz et al. |
| 2002/0183324 A1 | 12/2002 | Jacobson et al. |
| 2004/0082619 A1 | 4/2004 | Tada et al. |
| 2005/0266473 A1 | 12/2005 | Zhang et al. |
| 2008/0182844 A1 | 7/2008 | Bjergarde et al. |
| 2008/0222741 A1 | 9/2008 | Chinnaiyan |
| 2008/0269289 A1 | 10/2008 | Frank et al. |
| 2008/0312292 A1 | 12/2008 | Yasui et al. |
| 2009/0012031 A1 | 1/2009 | Chinnaiyan et al. |
| 2009/0061443 A1 | 3/2009 | Zhang et al. |
| 2009/0203057 A1 | 8/2009 | Zhang et al. |
| 2010/0035912 A1 | 2/2010 | Debnath et al. |
| 2010/0113415 A1 | 5/2010 | Rajapakse et al. |
| 2011/0021362 A1 | 1/2011 | Trojer et al. |
| 2012/0264734 A1 | 10/2012 | Kuntz et al. |
| 2013/0040906 A1 | 2/2013 | Kuntz et al. |
| 2015/0065503 A1 | 3/2015 | Kuntz et al. |
| 2015/0353494 A1 | 12/2015 | Kuntz et al. |
| 2016/0022693 A1 | 1/2016 | Kuntz et al. |

FOREIGN PATENT DOCUMENTS

| | | |
|---|---|---|
| WO | WO 1996/040100 | 12/1996 |
| WO | WO 2000/018725 | 4/2000 |
| WO | WO 2003/079788 | 10/2003 |
| WO | WO 2006/116713 | 11/2006 |
| WO | WO 2007/045462 | 4/2007 |
| WO | WO 2007/050347 | 5/2007 |
| WO | WO 2007/070818 | 6/2007 |
| WO | WO 2007/136592 | 11/2007 |
| WO | WO 2008/073138 | 6/2008 |
| WO | WO 2008/103277 | 8/2008 |
| WO | WO 2008/104077 | 9/2008 |
| WO | WO 2008/108825 | 9/2008 |
| WO | WO 2008/113006 | 9/2008 |
| WO | WO 2009/058298 | 5/2009 |
| WO | WO 2009/077766 | 6/2009 |
| WO | WO 2009/124137 | 10/2009 |
| WO | WO 2010/018328 | 2/2010 |
| WO | WO 2010/111653 | 9/2010 |
| WO | WO 2011/082044 | 7/2011 |
| WO | WO 2011/140324 | 11/2011 |
| WO | WO 2011/140325 | 11/2011 |
| WO | WO 2012/005805 | 1/2012 |
| WO | WO 2012/034132 | 3/2012 |
| WO | WO 2012/068589 | 5/2012 |
| WO | WO 2012/075080 | 6/2012 |
| WO | WO 2013/138361 A1 | 9/2013 |
| WO | WO 2013/155317 A1 | 10/2013 |
| WO | WO 2013/173441 | 11/2013 |

OTHER PUBLICATIONS

Chemical Abstracts Service Registry Nos. 1111568-29-6, 1111508-57-6, and 1111473-93-8 entered Feb. 25, 2009, 2 pages.

Chemical Abstracts Service Registry Nos. 1118856-92-0, 1118847-80-5, 1118847-59-8, 1118826-65-5, 1118826-02-0, 1118825-96-9, 1118825-75-4, 1118825-72-1, and 1118825-69-6 entered Mar. 11, 2009, 4 pages.

Chemical Abstracts Service Registry Nos. 1278089-60-3, 1277914-52-9, and 1277529-83-5, entered Apr. 10, 2011, 2 pages.

Chemical Abstracts Service Registry Nos. 1278854-92-4 and 127885491-3, entered Apr. 12, 2011, 1 page.

Chemical Abstracts Service Registry Nos. 919939-47-2 and 919873-05-5 entered Feb. 8, 2007, 1 page.

Chemical Abstracts Service Registry Nos. 923162-97-4, 923152-74-3, and 923111-85-7 entered Feb. 26, 2007, 2 pages.

Chemical Abstracts Service Registry Nos. 923774-47-4, 923730-10-3, and 923690-12-4 entered Feb. 28, 2007, 2 pages.

Chemical Abstracts Service Registry Nos. 941139-86-2 and 941091-93-6 entered Jul. 4, 2007, 1 page.

Gura et al. "Systems for Identifying New Drugs are Often Faulty." Science, 278:5340(1997), 1041-1042.

Johnson et al. "Relationships Between Drug Activity in NCI Preclinical in vitro and in vivo Models and Early Clinical Trials." Brit. J. Cancer. 84:10(2001),1424-1431.

Knutson et al. "A Selective Inhibitor of EZH2 Blocks H3K27 Methylation and Kills Mutant Lymphoma Cells." Nat. Chem. Biol. (2012):1-7. Epub: Sep. 30, 2012.

Lohr et al. "Discovery and Prioritization of Somatic Mutations in Diffuse Large B-Cell Lymphoma (DLBCL) by Whole-Exome Sequencing." PNAS. 109.10(2012):3879-3884. Epub Feb. 17, 2012.

Martinez-Garcia et al. "The MMSET Histone Methyl Transferase Switches Global Histone Methylation and Alters Gene Expression in t(4;14) Multiple Myeloma Cells." Blood. 117:1 (2011), 211-220.

McCabe et al. "EZH2 Inhibition as a Therapeutic Strategy for Lymphoma With EZH2-Activating Mutations." Nature. Epub: Oct. 10, 2012.

McCabe et al. "Mutation of A677 in Histone Methyltransferase EZH2 in Human B-Cell Lymphoma Promotes Hypertrimethylation of Histone H3 on Lysine 27 (H3K27)." PNAS.109:8(2012), 2989-2994.

Miranda et al. "DZNep is a Global Histone Methylation Inhibitor That Reactivates Developmental Genes not Silenced by DNA Methylation." Mol. Cancer Ther. 8:6(2009), 1579-1588.

Morin et al. "Somatic Mutations Altering EZH2 (Tyr641) in Follicular and Diffuse Large B-Cell Lymphomas of Germinal-Center Origin." Nat. Genet. 42:2(2010), 181-185.

Pearce et al. "Failure Modes in Anticancer Drug Discovery and Development." Cancer Drug Design and Discovery. Neidle, ed. Boston: Elsevier. (2008),424-435.

Sculley et al. "Some Amide Derivatives of Certain Aminomethylpyridines." J. Am. Chem. Soc. 75:14(1953), 3400-3403.

Simone. "Oncology: Introduction." Cecil Textbook of Medicine. Bennett et al., eds. Philadelphia: W. B. Saunders Co. 20th ed. 1, (1996), 1004-1008.

Sneeringer et al. "Coordinated Activities of Wild-Type Plus Mutant EZH2 Drive Tumor-Associated Hypertrimethylation of Lysine 27 on Histone H3 (H3K27) in Human B-Cell Lymphomas." PNAS. 107:49(2010), 20980-20985.

Wigle et al. "The Y641 C Mutation of EZH2 Alters Substrate Specificity for Histone H3 Lysine 27 Methylation States." FEBS Lett. 585:19(2011), 3011-3014.

Wilson et al. "Epigenetic Antagonism Between Polycomb and SWI/SNF Complexes During Oncogenic Transformation." Cancer Cell. 18(2010):316-328.

Yap et al. "Somatic Mutations at EZH2 Y641 Act Dominantly Through a Mechanism of Selectively Altered PRC2 Catalytic Activity, to Increase H3K27 Trimethylation." Blood. 117:.8(2010), 2451-2459.

The Japanese Pharmacopoeia, Sixteenth Edition, 2011, pp. 64-68 2.58 X-ray powder diffraction method, p. 2070.

HYDROCHLORIDE SALT FORM FOR EZH2 INHIBITION

RELATED APPLICATIONS

This application is a U.S. National Phase application, filed under 35 U.S.C. § 371, of International Application No. PCT/US2014/060724, filed Oct. 15, 2014, which claims priority to, and the benefit of, U.S. Provisional Application No. 61/891,786, filed Oct. 16, 2013, the contents of each of which are incorporated herein by reference in their entireties.

TECHNICAL FIELD

This disclosure relates to solid crystalline forms of N-((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide hydrochloride, and related compositions and methods.

BACKGROUND OF THE INVENTION

More than 1.6 million people are estimated to be diagnosed with cancer in 2013. For example, one of the most common types of cancer in women is breast cancer, and this disease is responsible for one of the highest fatality rates of all cancers affecting females. The current treatment of breast cancer is limited to total, or partial, mastectomy, radiation therapy, or chemotherapy. More than 232,340 cancer cases in 2013 will be breast cancer, which will result in an estimated 40,030 deaths. See, Siegel et al., CA: Cancer J. Clin. 2013; 63:11-30.

A number of cancer deaths are caused by blood cancers including leukemias, myelomas, and lymphomas. In 2013, almost 80,000 cancer cases will be lymphomas, estimated to result in over 20,000 deaths.

Radiation therapy, chemotherapy, and surgery are the primary methods of cancer treatment. However, these therapies are most successful only when the cancer is detected at an early stage. Once cancer reaches invasive/metastatic stages, lines of invading cells or metastasizing cells can escape detection, thus resulting in relapses, which requires the use of therapy that is highly toxic. At this point, both the cancer cells and the patient's unaffected cells are exposed to the toxic therapy, resulting with, among other complications, a weakening of the immune system. As such, there remains a need in the art for new methods for treating cancer, such as breast cancer or lymphoma, in a patient.

SUMMARY OF THE INVENTION

Accordingly, provided herein are novel solid forms (e.g., crystalline forms) of N-((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide hydrochloride:

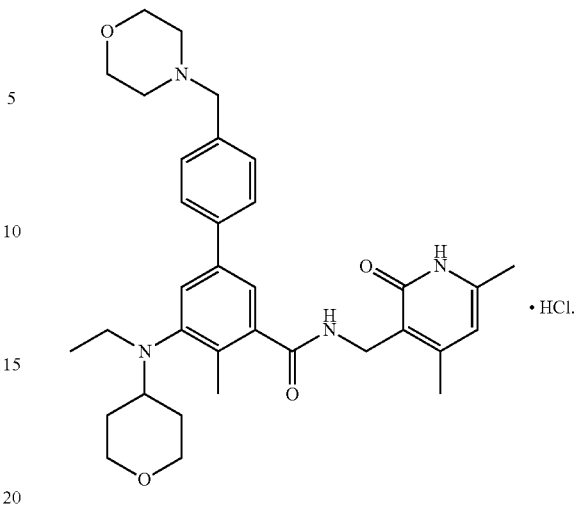

One embodiment of the invention is directed to Polymorph C of N-((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide hydrochloride. In one embodiment, Polymorph C is substantially free of impurities, meaning there is not a significant amount of impurities present in the sample of Polymorph C. In another embodiment, Polymorph C is a crystalline solid substantially free of amorphous N-((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide (or any of its amorphous mono- or multi-HCl forms). The skilled artisan understands that a solid sample of Polymorph C may also include Polymorph A, Polymorph B, and/or amorphous N-((4,6-dimethyl-2-oxo-1,2-dihydropyridin-3-yl)methyl)-5-(ethyl (tetrahydro-2H-pyran-4-yl)amino)-4-methyl-4'-(morpholinomethyl)-[1,1'-biphenyl]-3-carboxamide (or any of its amorphous mono- or multi-HCl forms).

Polymorph C of N-((4,6-dimethyl-2-oxo-1,2-dihydropyridin-3-yl)methyl)-5-(ethyl (tetrahydro-2H-pyran-4-yl)amino)-4-methyl-4'-(morpholinomethyl)-[1,1'-biphenyl]-3-carboxamide hydrochloride can be defined according to its X-ray powder diffraction pattern. Accordingly, in one embodiment, Polymorph C exhibits an X-ray powder diffraction pattern having characteristic peaks expressed in degrees 2-theta (+/−0.2) at 17.53, 18.66, 21.14, 22.22, 23.46, 27.72 and 30.30.

In one embodiment, Polymorph C exhibits an X-ray powder diffraction pattern having peaks with 2-theta values substantially in accordance with FIG. 3. In another embodiment, Polymorph C exhibits an X-ray powder diffraction pattern having peaks with 2-theta values substantially in accordance with Table 3.

Polymorph C can also be defined according to its differential scanning calorimetry thermogram. In one embodiment, the polymorph exhibits a differential scanning calorimetry thermogram showing a primary endotherm expressed in units of ° C. at a temperature of 228+/−5° C. In another embodiment, Polymorph C exhibits a differential scanning calorimetry thermogram substantially in accordance with the lowermost plot shown in FIG. 4 (i.e., "Polymorph C" plot).

Another aspect of the invention relates to the preparation of Polymorph C using a method comprising combining N-((4,6-dimethyl-2-oxo-1,2-dihydropyridin-3-yl)methyl)-5-

(ethyl (tetrahydro-2H-pyran-4-yl)amino)-4-methyl-4'-(morpholinomethyl)-[1,1'-biphenyl]-3-carboxamide with hydrochloric acid.

Another aspect of the invention relates to the preparation of, provided herein is a method of recrystallizing Polymorph C, which comprises the following steps: (a) dissolving Polymorph C in a first solvent to obtain a first solution, and (b) adding a second solvent to the first solution, such that said polymorph is recrystallized.

In still another aspect, provided herein is a pharmaceutical composition comprising Polymorph C, and optionally a pharmaceutically acceptable carrier or diluent. In one embodiment, the pharmaceutical composition comprises Polymorph C and a pharmaceutically acceptable carrier or diluent.

Also provided herein is a method of treating an EZH2-mediated cancer comprising administering to a subject in need thereof a therapeutically effective amount of Polymorph C, or a pharmaceutical composition thereof. A variety of EZH2-mediated cancers may be treated with Polymorph C, including non-Hodgkin's lymphoma, B cell lymphoma including diffuse large B cell lymphoma (DLBCL), follicular lymphoma, or solid tumors including breast cancer.

In another aspect, provided herein is a method of inhibiting the histone methyltransferase activity of EZH2 in a subject in need thereof comprising administering to the subject an effective amount of Polymorph C, or a pharmaceutical composition thereof.

In still another aspect, provided herein is a method of inhibiting the histone methyltransferase activity of EZH2 in vitro comprising administering Polymorph C or a pharmaceutical composition thereof.

Also provided herein is the use of Polymorph C, or a pharmaceutical composition thereof, for the preparation of a medicament for the treatment of an EZH2-mediated cancer in a subject in need thereof.

Another aspect of this invention is a method of treating or preventing an EZH2-mediated disorder. The method includes administering to a subject in need thereof a therapeutically effective amount of one or more polymorphs disclosed herein. The EZH2-mediated disorder is a disease, disorder, or condition that is mediated at least in part by the activity of EZH2. In one embodiment, the EZH2-mediated disorder is related to an increased EZH2 activity. In one embodiment, the increased EZH2 activity is due to a mutation in the SET domain of EZH2. In one embodiment, the mutation is at Y641, A677, or A687, or a combination thereof. In one embodiment, the EZH2 mutation increases trimethylation of Lys27 of histone H3 (H3-K27). In one embodiment, the EZH2-mediated disorder is a cancer. The EZH2-mediated cancer may be lymphoma, leukemia or melanoma, for example, diffuse large B-cell lymphoma (DLBCL), non-Hodgkin's lymphoma (NHL), follicular lymphoma, chronic myelogenous leukemia (CML), acute myeloid leukemia, acute lymphocytic leukemia, mixed lineage leukemia, or myelodysplastic syndromes (MDS). In one embodiment the EZH2-mediated cancer may be a malignant rhabdoid tumor or INI1-defecient tumor. The histologic diagnosis of malignant rhabdoid tumor depends on identification of characteristic rhabdoid cells (large cells with eccentrically located nuclei and abundant, eosinophilic cytoplasm) and immunohistochemistry with antibodies to vimentin, keratin and epithelial membrane antigen. In most malignant rhabdoid tumors, the SMARCB1/INI1 gene, located in chromosome band 22q11.2, is inactivated by deletions and/or mutations. In one embodiment, the malignant rhabdoid tumors may be INI1-defecient tumor.

Unless otherwise stated, any description of a method of treatment includes uses of the polymorphs to provide such treatment or prophylaxis as is described in the specification, as well as uses of the polymorphs to prepare a medicament to treat or prevent such condition. The treatment includes treatment of human or non-human animals including rodents and other disease models.

Further, the polymorphs or methods described herein may be used for research (e.g., studying epigenetic enzymes) and other non-therapeutic purposes.

DETAILED DESCRIPTION OF THE INVENTION

The solid form (e.g., crystal state) of a compound may be important when the compound is used for pharmaceutical purposes. Compared with an amorphous solid, the solid physical properties of a crystalline compound may change from one solid form to another, which may impact its suitability for pharmaceutical use. In addition, different solid forms of a crystalline compound may incorporate different types and/or different amounts of impurities. Different solid forms of a compound may also have different chemical stability upon exposure to heat, light and/or moisture (e.g., atmospheric moisture) over a period of time, or different rates of dissolution. There remains a need for solid crystalline forms of N-((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide that are not hygroscopic, and that exhibit improved chemical stability for use in drug substance and drug product development.

Provided herein are novel crystalline forms of N-((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide hydrochloride:

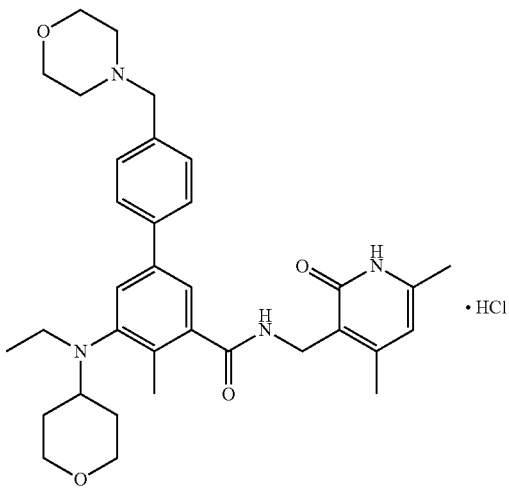 [SMILES: CCN(c1cc(-c2ccc(CN3CCOCC3)cc2)cc(C(=O)NCc2c(C)cc(C)[nH]c2=O)c1C)C1CCOCC1 ; "· HCl"]

Described herein are polymorphic forms A, B and C of N-((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide hydrochloride (also referred to herein respectively as "Polymorph A", "Polymorph B" and "Polymorph C").

As used herein, "Compound I" refers to N-((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide. The hydrochloride (i.e., hydrochloride salt) of Compound I may be used to inhibit the histone methyltransferase activity of EZH2, either in a subject or in vitro. The hydrochloride of Compound I may also be used to treat EZH2-mediated cancer in a subject in need thereof.

Compound I can be protonated at one or more of its basic sites, such as the morpholine, disubstituted aniline, and/or pyridone moieties. The compound may be protonated at any basic site. Without being limited to the following, it is believed that Compound I is protonated at the nitrogen of the morpholino substituent, providing a hydrochloride of Compound I having the following structure:

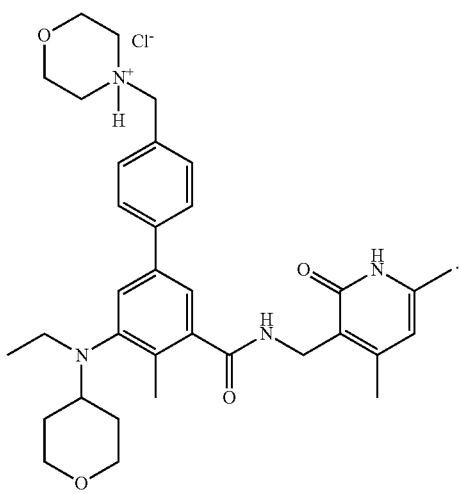 [SMILES: CCN(c1cc(-c2ccc(C[NH+]3CCOCC3)cc2)cc(C(=O)NCc2c(C)cc(C)[nH]c2=O)c1C)C1CCOCC1 ; [Cl-] ; "."]

Figure 3:
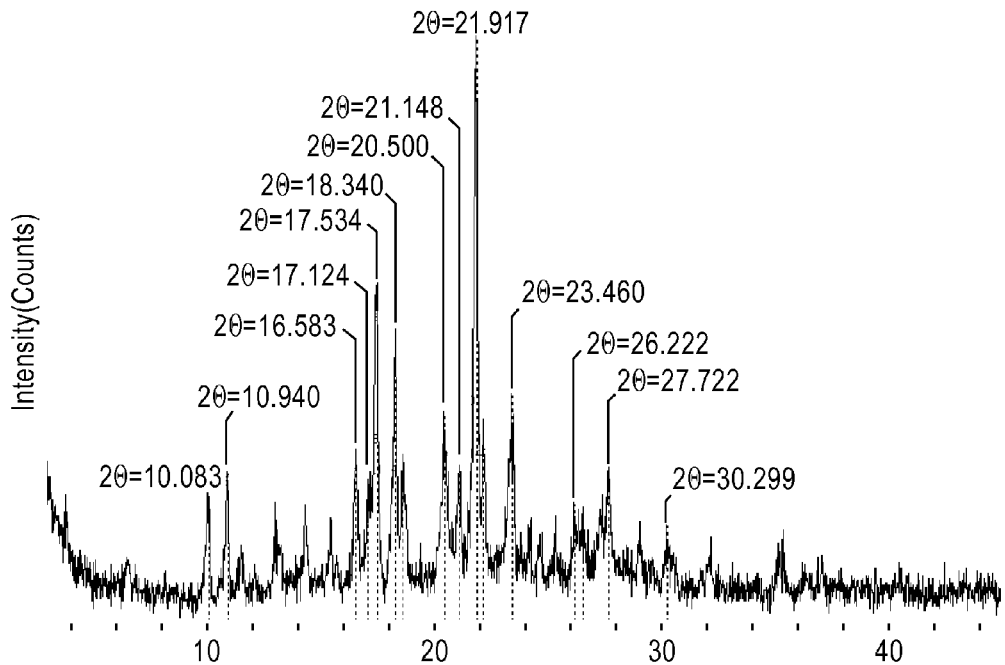
FIG. 3 depicts a representative X-ray powder diffraction pattern of Polymorph C.
Figure 4:
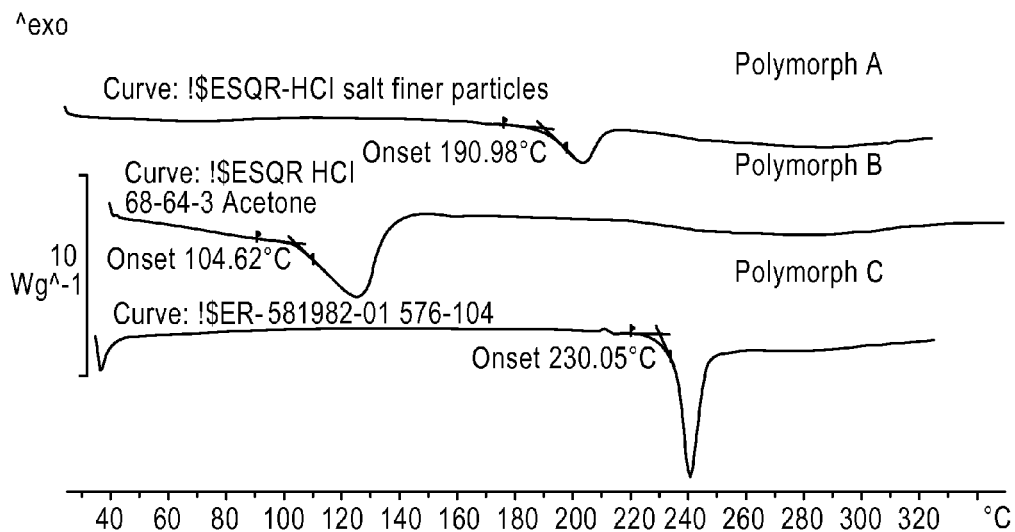
FIG. 4 depicts differential scanning calorimetry (DSC) data for Polymorphs A, B and C.
Figure 5:
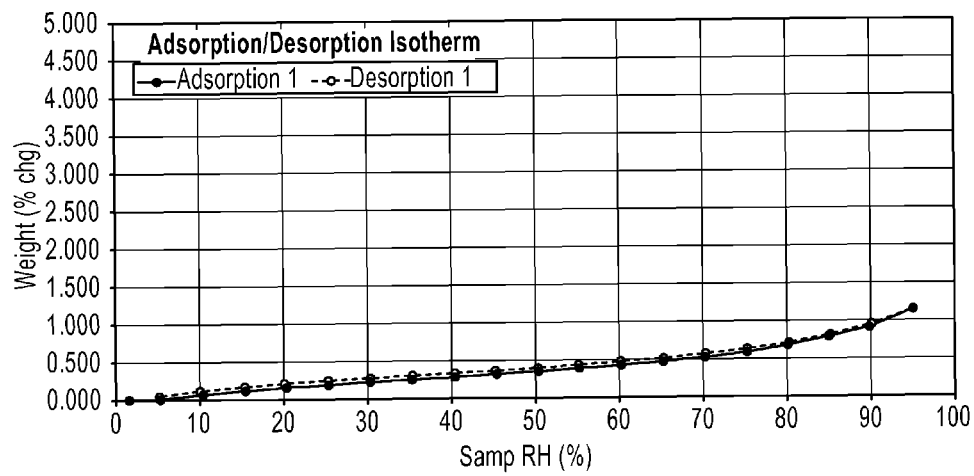
FIG. 5 depicts dynamic vapor sorption (DVS) data for Polymorph C.

If there is any discrepancy as to the identity of Polymorph C as between (i) the above structure and (ii) the compound identified by the data of FIGS. 3, 5 and the lowest plot depicted in FIG. 4, the latter (i.e., Figures of (ii)) shall control.

The monohydrochloride drawn in the preceding paragraph can be referred to as "4-((3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)methyl)morpholin-4-ium chloride." The monohydrochloride salt of N-((4,6-dimethyl-2-oxo-1,2-dihydropyridin-3-yl)methyl)-5-(ethyl (tetrahydro-2H-pyran-4-yl)amino)-4-methyl-4'-(morpholinomethyl)-[1,1'-biphenyl]-3-carboxamide can be produced in a highly crystalline form, which is useful in the preparation of pharmaceutical formulations, and will improve general handling, manipulation, and storage of the drug compound. In a preferred embodiment, the crystalline form of the hydrochloride salt of Compound I is in a form referred to as "Polymorph C." As described herein, Polymorph C exhibits physical properties that can be exploited in order to obtain new pharmacological properties, and that may be utilized in drug substance and drug product development.

The ability of a substance to exist in more than one crystal form is defined as polymorphism; the different crystal forms of a particular substance are referred to as "polymorphs" of one another. In general, polymorphism is affected by the ability of a molecule of a substance (or its salt or hydrate) to change its conformation or to form different intermolecular or intra-molecular interactions, (e.g., different hydrogen bond configurations), which is reflected in different atomic arrangements in the crystal lattices of different polymorphs. In contrast, the overall external form of a substance is known as "morphology," which refers to the external shape of the crystal and the planes present, without reference to the internal structure. A particular crystalline polymorph can display different morphology based on different conditions, such as, for example, growth rate, stirring, and the presence of impurities.

The different polymorphs of a substance may possess different energies of the crystal lattice and, thus, in solid state they can show different physical properties such as form, density, melting point, color, stability, solubility, dissolution rate, etc., which can, in turn, effect the stability, dissolution rate and/or bioavailability of a given polymorph and its suitability for use as a pharmaceutical and in pharmaceutical compositions.

Polymorph C has a number of advantageous physical properties over its free base form, as well as other salts of the free base. In particular, Polymorph C has low hygroscopicity compared to other salt forms of Compound I. More particularly, Polymorph C has low hygroscopicity compared to Polymorph A (i.e., another polymorph form of N-((4,6-dimethyl-2-oxo-1,2-dihydropyridin-3-yl)methyl)-5-(ethyl (tetrahydro-2H-pyran-4-yl)amino)-4-methyl-4'-(morpholinomethyl)-[1,1'-biphenyl]-3-carboxamide hydrochloride) (see, e.g., FIGS. 5 and 6). For consistency with drug formulation (e.g., tableting), it is generally required that the polymorphic form of the active pharmaceutical ingredient (API) compound be minimally hygroscopic. Drug forms that are highly hygroscopic may also be unstable, as the drug form's dissolution rate (and other physico-chemical properties) may change as it is stored in settings with varying humidity. Also, hygroscopicity can impact large-scale handling and manufacturing of a compound, as it can be difficult to determine the true weight of a hygroscopic active agent when preparing a pharmaceutical composition comprising that agent. For example, in large scale tableting or other medicinal formulating preparations, highly hygroscopic compounds can result in batch manufacturing inconsistency creating clinical and/or prescribing difficulties. Polymorph C has a low hygoscopicity compared to other salt forms of Compound I. As such, it may be stored over appreciable periods or conditions (e.g., relative humidity conditions), and not suffer from detrimental formulating changes.

In certain embodiments, Polymorph C is identifiable on the basis of characteristic peaks in an X-ray powder diffraction analysis. X-ray powder diffraction pattern, also referred to as XRPD pattern, is a scientific technique involving the scattering of x-rays by crystal atoms, producing a diffraction pattern that yields information about the structure of the crystal. In certain embodiments, Polymorph C exhibits an X-ray powder diffraction pattern having from two (2) to seven (7) characteristic peaks expressed in degrees 2-theta at 17.53, 18.66, 21.14, 22.22, 23.46, 27.72 and 30.30.

The skilled artisan recognizes that some variation is associated with 2-theta measurements. Typically, 2-theta values may vary from ±0.1 to ±0.2. Such slight variation can be caused, for example, by sample preparation and other experimental factors. The skilled artisan appreciates that such variation in values are greatest with low 2-theta values, and least with high 2-theta values. The skilled artisan recognizes that different instruments may provide substantially the same XRPD pattern, even though the 2-theta values vary somewhat. Moreover, the skilled artisan appreciates that the same instrument may provide substantially the same XRPD pattern for the same or different samples even though the XRPD of the respectively collected XRPD patterns vary slightly in the 2-theta values.

The skilled artisan also appreciates that XRPD patterns of the same sample (taken on the same or different instruments) may exhibit variations in peak intensity at the different 2-theta values. The skilled artisan also appreciates that XRPD patterns of different samples of the same polymorph (taken on the same or different instruments) may also exhibit variations in peak intensity at the different 2-theta values. XRPD patterns can be substantially the same pattern even though they have corresponding 2-theta signals that vary in their peak intensities.

In one embodiment, Polymorph C exhibits an X-ray powder diffraction pattern having two or more characteristic peaks expressed in degrees 2-theta (+/−0.2) at 17.53, 18.66, 21.14, 22.22, 23.46, 27.72 and 30.30. In another embodiment, Polymorph C exhibits an X-ray powder diffraction pattern having three or more characteristic peaks expressed in degrees 2-theta (+/−0.2) at 17.53, 18.66, 21.14, 22.22, 23.46, 27.72 and 30.30. In another embodiment, Polymorph C exhibits an X-ray powder diffraction pattern having four or more characteristic peaks expressed in degrees 2-theta (+/−0.2) at 17.53, 18.66, 21.14, 22.22, 23.46, 27.72 and 30.30. In another embodiment, Polymorph C exhibits an X-ray powder diffraction pattern having characteristic peaks expressed in degrees 2-theta (+/−0.2) at 17.53, 21.14, 23.46 and 27.72.

In a particular embodiment, Polymorph C exhibits an X-ray powder diffraction pattern having at least eight characteristic peaks expressed in degrees 2-theta (+/−0.2), selected from the group consisting of 10.08, 10.94, 16.58, 17.12, 17.53, 18.34, 18.66, 20.50, 21.14, 21.92, 22.22, 23.46, 26.22, 26.60, 27.72, and 30.30. In another particular embodiment, Polymorph C exhibits an X-ray powder diffraction pattern having at least nine characteristic peaks expressed in degrees 2-theta (+/−0.2), selected from the group consisting of 10.08, 10.94, 17.12, 17.53, 18.34, 18.66, 20.50, 21.14, 21.92, 22.22, 23.46, 26.22, 26.60, 27.72, and 30.30.

In one embodiment, Polymorph C exhibits an X-ray powder diffraction pattern having a characteristic peaks expressed in degrees 2-theta (+/−0.2) at 27.72.

Pharmaceutical compositions comprising Polymorph C can be identified by comparison of the compositions' X-ray powder diffraction patterns to an X-ray powder diffraction pattern of Polymorph C. It will be appreciated that pharmaceutical compositions comprising Polymorph C may exhibit non-identical X-ray powder diffraction patterns that are substantially the same pattern as compared to FIG. 3. Observed slight differences in XRPD patterns may be attributed to the aforementioned factors, including the presence of other impurities in the sample.

In other embodiments of the invention, Polymorph C is identifiable on the basis of a characteristic peak observed in a differential scanning calorimetry thermogram. Differential scanning calorimetry, or DSC, is a thermoanalytical technique in which the difference in the amount of heat required to increase the temperature of a sample and reference is measured as a function of temperature. In one embodiment, Polymorph C exhibits a differential scanning calorimetry thermogram showing a characteristic peak expressed in units of ° C. with an onset temperature of about 230+/−5° C. In another embodiment, Polymorph C exhibits a differential scanning calorimetry thermogram showing a characteristic primary endotherm expressed in units of ° C. at a temperature of about 228+/−5° C. In another embodiment, Polymorph C exhibits a differential scanning calorimetry thermogram substantially in accordance with FIG. 4.

In another embodiment of the invention, provided herein is Polymorph C characterized as a solid form of N-((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide hydrochloride, wherein the solid form undergoes a weight increase of less than 1.5% upon increasing relative humidity from 5.0% to 95.0%. In another embodiment, Polymorph C is characterized as having a dynamic vapor sorption profile that is substantially in accordance with FIG. 5.

In certain embodiments, a sample of Polymorph C may contain impurities. Non-limiting examples of impurities include other polymorph forms, or residual organic and inorganic molecules such as related impurities (e.g., intermediates used to make Polymorph C or fragments thereof), solvents, water or salts. In one embodiment, a sample of Polymorph C is substantially free from impurities, meaning that no significant amount of impurities are present. In another embodiment, a sample of Polymorph C contains less than 10% weight by weight (wt/wt) total impurities. In another embodiment, a sample of Polymorph C contains less than 5% wt/wt total impurities. In another embodiment, a sample of Polymorph C contains less than 2% wt/wt total impurities. In another embodiment, a sample of Polymorph C contains less than 1% wt/wt total impurities. In yet another embodiment, a sample of Polymorph C contains less than 0.1% wt/wt total impurities.

In certain embodiments, a sample of Polymorph C is a crystalline solid substantially free of amorphous Compound I (or any of its amorphous mono- or multi-HCl forms). As used herein, the term "substantially free of amorphous Compound I" means that the compound contains no significant amount of amorphous Compound I (or any of its amorphous mono- or multi-HCl forms). In another embodiment, a sample of crystalline Compound I comprises Polymorph C substantially free of Polymorph A and/or B. As used herein, the term "substantially free of Polymorph A and/or B" means that a sample of crystalline Compound I hydrochloride contains no significant amount of Polymorph A and/or B. In certain embodiments, at least about 90% by weight of a sample is Polymorph C, with only 10% being Polymorph A and/or B and/or amorphous Compound I (or any of its amorphous mono- or multi-HCl forms). In certain embodiments, at least about 95% by weight of a sample is Polymorph C, with only 5% being Polymorph A and/or B and/or amorphous Compound I (or any of its amorphous mono- or multi-HCl forms). In still other embodiments of the invention, at least about 98% by weight of a sample is Polymorph C, with only 2% by weight being Polymorph A and/or B and/or amorphous Compound I (or any of its amorphous mono- or multi-HCl forms). In still other embodiments of the invention, at least about 99% by weight of a sample is Polymorph C, with only 1% by weight being Polymorph A and/or B and/or amorphous Compound I (or any of its amorphous mono- or multi-HCl forms). In still other embodiments of the invention, at least about 99.5% by weight of a sample is Polymorph C, with only 0.5% by weight being Polymorph A and/or B and/or amorphous Compound I (or any of its amorphous mono- or multi-HCl forms). In still other embodiments of the invention, at least about 99.9% by weight of a sample is Polymorph C, with only 0.1% by weight being Polymorph A and/or B and/or amorphous Compound I (or any of its amorphous mono- or multi-HCl forms).

Polymorph C may occur as any reasonable tautomer, or a mixture of reasonable tautomers. As used herein, "tautomer" refers to one of two or more structural isomers that exist in equilibrium and are readily converted from one isomeric form to another. Examples include keto-enol tautomers, such as acetone/propen-2-ol, and the like. Polymorph C may have one or more tautomers and therefore include various isomers, i.e., pyridin-2(1H)-one and the corresponding pyridin-2-ol. All such isomeric forms of these compounds are expressly included in the present invention.

Preparation of Polymorphs

General techniques for making polymorphs are understood by the skilled artisan. Conventionally, a salt form is prepared by combining in solution the free base compound and an acid containing the anion of the salt form desired, and then isolating the solid salt product from the reaction solution (e.g., by crystallization, precipitation, evaporation, etc.). Other salt-forming techniques may be employed.

Once a polymorph is prepared, it may be recrystallized, using the same solvent (or solvents) that were used to prepare the polymorph, or a different solvent (or solvents), to produce a composition that has increased crystallinity. In general, polymorphs may be recrystallized by dissolving the polymorph in one or more solvents, optionally heating, followed by an optional cooling step, and then isolating the crystal structure, through, e.g., a filtering step. After the polymorph is initially dissolved in the first solvent (or combination of solvents), an additional, different solvent may be added at any point in the process (before or after heating, before or after cooling, etc.) to produce the desired crystal structure. For example, a first solvent may be used to dissolve the polymorph compound, and then a second solvent (e.g., an anti-solvent) may be added to cause the polymorph to precipitate from solution.

Non-limiting examples of solvents that may be used for the recrystallization of polymorphs are as follows: methanol, ethanol, ethyl acetate, methyl tert-butyl ether, water, isopropyl alcohol, tetrahydrofuran, acetone, acetonitrile, and 2-methyltetrahydrofuran, as well as combinations thereof.

Non-limiting examples of solvent combinations that are useful for the recrystallization of polymorphs are (solvent and anti-solvent, wherein water can be added to the first solvent to aid in dissolving the polymorph): methanol/water and ethyl acetate, isopropyl alcohol/water and ethyl acetate, tetrahydrofuran/water and ethyl acetate, acetone and ethyl acetate, acetonitrile/water and ethyl acetate, ethanol/water and methyl tert-butyl ether, isopropyl alcohol/water and methyl tert-butyl ether, ethanol/water and tetrahydrofuran, isopropyl alcohol/water and acetone, and ethanol/water and ethyl acetate. In particular embodiments, the solvent combinations may be ethanol/water and ethyl acetate, methanol and ethyl acetate, and ethanol and ethyl acetate.

In one aspect, provided herein is a method of preparing Polymorph C of N-((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide hydrochloride comprising combining N-((4,6-dimethyl-2-oxo-1,2-dihydropyridin-3-yl)methyl)-5-(ethyl (tetrahydro-2H-pyran-4-yl)amino)-4-methyl-4'-(morpholinomethyl)-[1,1'-biphenyl]-3-carboxamide with hydrochloric acid.

In one embodiment, the method of making Polymorph C comprises the steps:

a) Dissolving N-((4,6-dimethyl-2-oxo-1,2-dihydropyridin-3-yl)methyl)-5-(ethyl (tetrahydro-2H-pyran-4-yl) amino)-4-methyl-4'-(morpholinomethyl)-[1,1'-biphenyl]-3-carboxamide in a first solvent to obtain a solution;

b) Combining hydrochloric acid with the solution;

c) Combining a second solvent with the solution;

d) Precipitating or crystallizing Polymorph C of N-((4,6-dimethyl-2-oxo-1,2-dihydropyridin-3-yl)methyl)-5-(ethyl (tetrahydro-2H-pyran-4-yl)amino)-4-methyl-4'-(morpholinomethyl)-[1,1'-biphenyl]-3-carboxamide monohydrochloride from the solution; and e) Collecting Polymorph C of N-((4,6-dimethyl-2-oxo-1, 2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide monohydrochloride.

In one embodiment of the method, the first solvent comprises ethanol. In another embodiment, the hydrochloric acid is in a concentrated aqueous solution. In still another embodiment, the second solvent comprises ethyl acetate. In other embodiments, one or more of the solutions of steps a), b) or c) is heated.

In an embodiment, water is added to the first solvent to aid in dissolving the polymorph.

In a particular embodiment of the method of making Polymorph C, a suspension of N-((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide (about 1 equivalent) in ethanol (about 1 volume) is heated, and treated with hydrochloric acid (about 1 equivalent). The mixture is stirred at elevated temperature, and is then treated with ethyl acetate (about 2 volumes). The resulting mixture is stirred at elevated temperature and is then slowly cooled to room temperature. The resulting precipitate is filtered, washed with ethyl acetate and dried to give Polymorph C.

In another aspect, provided herein is a method of recrystallizing Polymorph C, which comprises the following steps: (a) dissolving Polymorph C in a first solvent to obtain a first solution, and (b) adding a second solvent, such that said polymorph is recrystallized. In one embodiment, the method comprises (a) dissolving Polymorph C in ethanol, (b) heating the mixture, (c) adding ethyl acetate to the mixture, forming a precipitate comprising said polymorph, and filtering the precipitate such that said polymorph is recrystallized. In one embodiment, the first solvent is ethanol, and the second solvent is ethyl acetate. In another embodiment, the first solvent is ethanol and water, and the second solvent is ethyl acetate. In another embodiment, the first solvent is methanol, and the second solvent is ethyl acetate. In some embodiments, the method further comprises heating the first solution prior to adding the second solvent.

Figure 1:
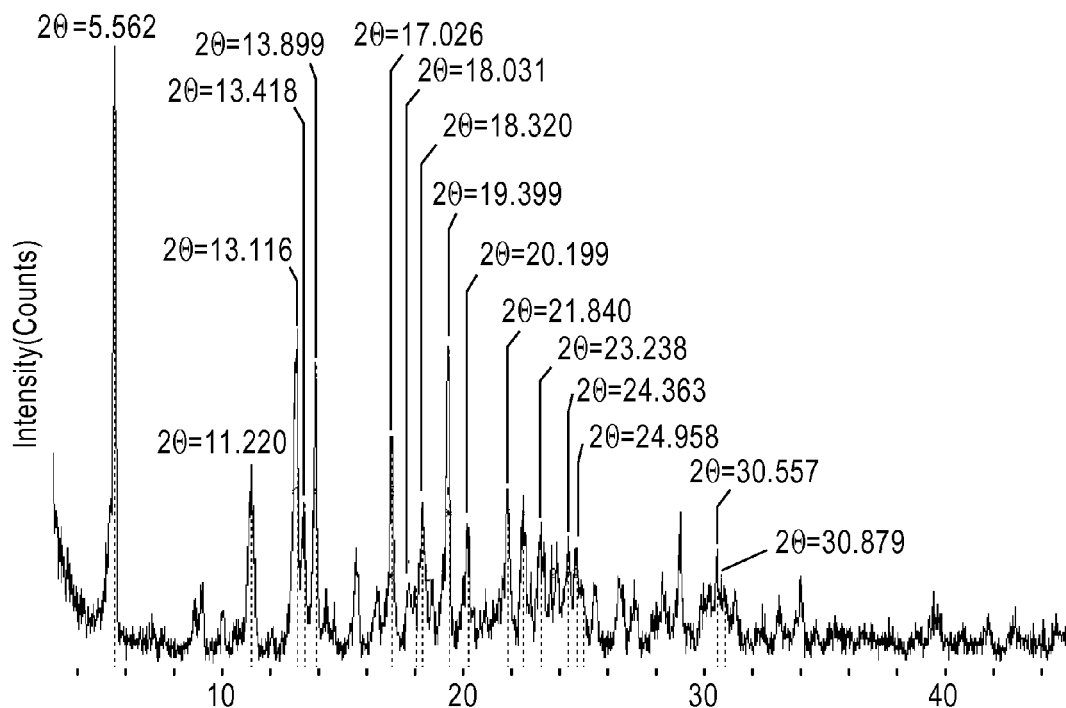
FIG. 1 depicts a representative X-ray powder diffraction pattern of Polymorph A.
Figure 2:
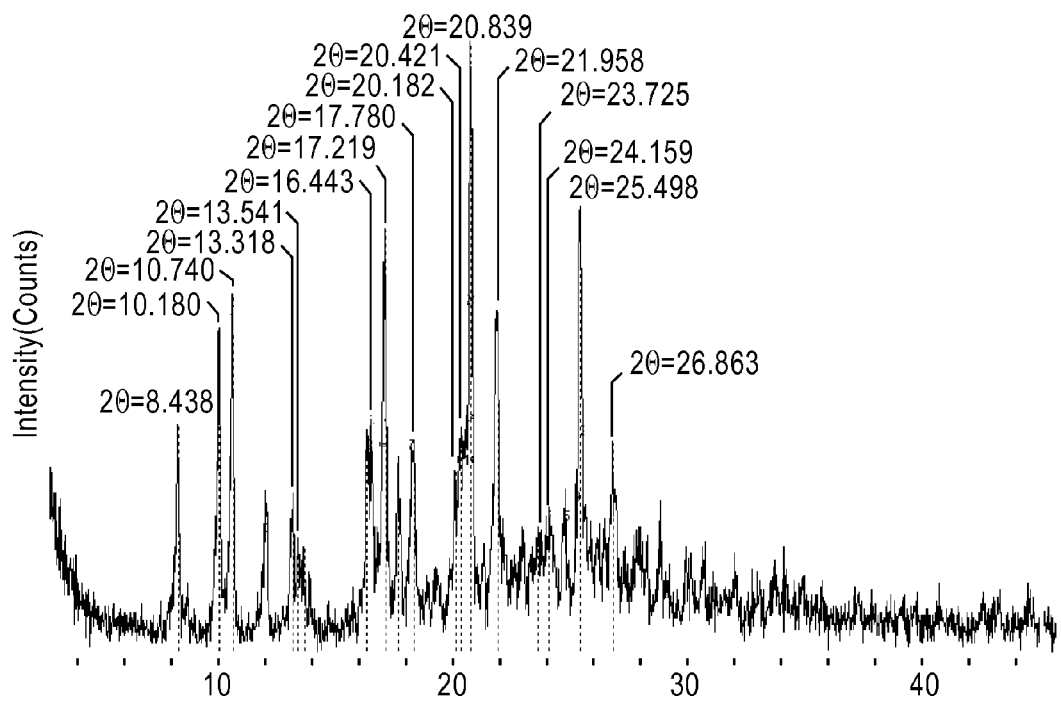
FIG. 2 depicts a representative X-ray powder diffraction pattern of Polymorph B.

In another aspect, provided herein is Polymorph B of N-((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide hydrochloride. In one embodiment, Polymorph B exhibits an X-ray powder diffraction pattern substantially in accordance with FIG. 2. In another embodiment, Polymorph B exhibits an X-ray powder diffraction pattern substantially in accordance with Table 2. In another embodiment, Polymorph B exhibits a differential scanning calorimetry thermogram having an onset temperature expressed in units of ° C. at a temperature of 105+/−5° C. In another embodiment, Polymorph B exhibits a DSC thermogram substantially in accordance with FIG. 4. In another embodiment, Polymorph B exhibits a DSC thermogram substantially in accordance with Table 4.

Pharmaceutical Compositions

In another aspect, provided herein is a pharmaceutical composition comprising polymorphs of the present invention (e.g., Polymorph C), and optionally a pharmaceutically acceptable carrier or diluent. Also provided herein is a pharmaceutical composition comprising polymorphs of the present invention (e.g., Polymorph C) and a pharmaceutically acceptable carrier or diluent.

The term "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1% to 99.9% (more preferably, 0.5 to 90%) of active ingredient in combination with a pharmaceutically acceptable carrier.

The polymorphs described herein (e.g., Polymorph C) may be combined with a pharmaceutically acceptable carrier according to conventional pharmaceutical compounding techniques. As used herein, "pharmaceutically acceptable carrier" may include any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Furthermore, the carrier may take a wide variety of forms depending on the form of the preparation desired for administration, e.g. oral, nasal, rectal, vaginal, parenteral (including intravenous injections or infusions). In preparing compositions for oral dosage form any of the usual pharmaceutical media may be employed. Usual pharmaceutical media include, for example, water, glycols, oils, alcohols, flavoring agents, preservatives, coloring agents, and the like in the case of oral liquid preparations (such as for example, suspensions, solutions, emulsions and elixirs); aerosols; or carriers such as starches, sugars, microcrystalline cellulose, diluents, granulating agents, lubricants, binders, disintegrating agents and the like, in the case of oral solid preparations (such as for example, powders, capsules, and tablets).

Pharmaceutical compositions comprising the polymorphs of the present invention (e.g., Polymorph C) may be formulated to have any concentration desired. In some embodiments, the composition is formulated such that it comprises at least a therapeutically effective amount. As used herein, "therapeutically effective amount" means that amount necessary to make a clinically observed improvement in the patient. In some embodiments, the composition is formulated such that it comprises an amount that would not cause one or more unwanted side effects.

Pharmaceutical compositions include those suitable for oral, sublingual, nasal rectal, vaginal, topical, buccal and parenteral (including subcutaneous, intramuscular, and intravenous) administration, although the most suitable route will depend on the nature and severity of the condition being treated. The compositions may be conveniently presented in unit dosage form, and prepared by any of the methods well known in the art of pharmacy. In certain embodiments, the pharmaceutical composition is formulated for oral administration in the form of a pill, capsule, lozenge or tablet. In other embodiments, the pharmaceutical composition is in the form of a suspension.

The compounds provided herein are suitable as an active agent in pharmaceutical compositions that are efficacious particularly for treating EZH2-associated disorders, especially cancer. The pharmaceutical composition in various embodiments has a pharmaceutically effective amount of a polymorph of the present invention (e.g., Polymorph C), along with other pharmaceutically acceptable excipients, carriers, fillers, diluents and the like.

A therapeutically or pharmaceutically "effective amount" is an amount of a polymorph of the present invention (e.g., Polymorph C), that when administered to a patient, ameliorates a symptom of an EZH2-mediated disease or condition, e.g., prevent the various morphological and somatic symptoms of an EZH2-mediated cancer. The amount can vary depending on such factors as the size and weight of the subject, the type of illness, or the particular compound of the invention. The amount of a polymorph of the present invention (e.g., Polymorph C) that constitutes an "effective amount" will vary depending on the compound, the disease state and its severity, the age of the patient to be treated, and the like. The effective amount can be determined routinely by one of ordinary skill in the art having regard to their knowledge and to this disclosure.

The regimen of administration can affect what constitutes a pharmaceutically effective amount. A polymorph of the present invention (e.g., Polymorph C), and compositions thereof, can be administered to the subject either prior to or after the onset of a disease. Further, several divided dosages, as well as staggered dosages can be administered daily or sequentially, or the dose can be continuously infused, or can be a bolus injection. Further, the dosages can be proportionally increased or decreased as indicated by the exigencies of the therapeutic or prophylactic situation. Further, the dosages may be co-administered in combination with other chemotherapeutic agents known by the skilled artisan.

Methods of Treatment

Polymorphs of the present invention (e.g., Polymorph C) inhibit the histone methyltransferase activity of EZH2 or a mutant thereof and, accordingly, in one aspect of the invention, certain polymorphs disclosed herein are candidates for treating, or preventing certain conditions and diseases in which EZH2 plays a role. The present invention provides methods for treating conditions and diseases the course of which can be influenced by modulating the methylation status of histones or other proteins, wherein said methylation status is mediated at least in part by the activity of EZH2. Modulation of the methylation status of histones can in turn influence the level of expression of target genes activated by methylation, and/or target genes suppressed by methylation. The method includes administering to a subject in need of such treatment, a therapeutically effective amount of a polymorph of the present invention (e.g., Polymorph C).

Unless otherwise stated, any description of a method of treatment includes uses of the polymorphs to provide such treatment or prophylaxis as is described in the specification, as well as uses of the polymorphs to prepare a medicament to treat or prevent such condition. The treatment includes treatment of human or non-human animals including rodents and other disease models.

In still another aspect, this invention relates to a method of modulating the activity of the EZH2, the catalytic subunit of the PRC2 complex which catalyzes the mono- through trimethylation of lysine 27 on histone H3 (H3-K27) in a subject in need thereof. For example, the method comprises the step of administering to a subject having a cancer expressing a mutant EZH2 (e.g., a Y641 mutant of EZH2) a therapeutically effective amount of a polymorph described herein, wherein the polymorph inhibits histone methyltransferase activity of EZH2, thereby treating the cancer.

For example, the EZH2-mediated cancer is selected from the group consisting of follicular lymphoma and diffuse large B-cell lymphoma (DLBCL) of germinal center B cell-like (GCB) subtype. For example, the cancer is lymphoma, leukemia or melanoma. Preferably, the lymphoma is non-Hodgkin's lymphoma (NHL), follicular lymphoma or diffuse large B-cell lymphoma. Alternatively, the leukemia is chronic myelogenous leukemia (CML), acute myeloid leukemia, acute lymphocytic leukemia or mixed lineage leukemia.

For example, the EZH2-mediated precancerous condition is myelodysplastic syndromes (MDS, formerly known as preleukemia).

For example, the EZH2-mediated cancer is a hematological cancer.

The polymorph of the present invention (e.g., Polymorph C) inhibits the histone methyltransferase activity of EZH2 or a mutant thereof and, accordingly, the present invention also provides methods for treating conditions and diseases the course of which can be influenced by modulating the methylation status of histones or other proteins, wherein said methylation status is mediated at least in part by the activity of EZH2. In one aspect of the invention, certain polymorphs disclosed herein are candidates for treating, or preventing certain conditions and diseases. Modulation of the methylation status of histones can in turn influence the level of expression of target genes activated by methylation, and/or target genes suppressed by methylation. The method includes administering to a subject in need of such treatment, a therapeutically effective amount of a polymorph of the present invention.

As used herein, a "subject" is interchangeable with a "subject in need thereof", both of which refer to a subject having a disorder in which EZH2-mediated protein methylation plays a part, or a subject having an increased risk of developing such disorder relative to the population at large. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human. A subject in need thereof can be one who has been previously diagnosed or identified as having cancer or a precancerous condition. A subject in need thereof can also be one who has (e.g., is suffering from) an EZH2-mediated cancer or an EZH2-mediated precancerous condition. Alternatively, a subject in need thereof can be one who has an increased risk of developing such disorder relative to the population at large (i.e., a subject who is predisposed to developing such disorder relative to the population at large). A subject in need thereof can have an EZH2-mediated precancerous condition. A subject in need thereof can have refractory or resistant EZH2-mediated cancer (i.e., cancer that doesn't respond or hasn't yet responded to treatment). The subject may be resistant at start of treatment or may become resistant during treatment. In some embodiments, the subject in need thereof has cancer recurrence following remission on most recent therapy. In some embodiments, the subject in need thereof received and failed all known effective therapies for cancer treatment. In some embodiments, the subject in need thereof received at least one prior therapy. In a preferred embodiment, the subject has an EZH2-mediated cancer or an EZH2-mediated cancerous condition. For example, the EZH2-mediated cancer is lymphoma, leukemia, melanoma, or rhabdomyosarcoma. Preferably, the lymphoma is non-Hodgkin's lymphoma, follicular lymphoma or diffuse large B-cell lymphoma. Alternatively, the leukemia is chronic myelogenous leukemia (CML). The precancerous condition is myelodysplastic syndromes (MDS, formerly known as preleukemia).

As used herein, "treating," "treatment" or "treat" describes the management and care of a patient for the purpose of combating a disease, condition, or disorder and includes the administration of a polymorph of the present invention (e.g., Polymorph C), to alleviate the symptoms or complications of a disease, condition or disorder, or to eliminate the disease, condition or disorder. The term "treat" can also include treatment of a cell in vitro or an animal model.

A polymorph of the present invention may also be used to prevent a relevant disease, condition or disorder, or used to identify suitable candidates for such purposes. As used herein, "preventing," "prevent," or "protecting against" describes reducing, ameliorating or eliminating the onset of the symptoms or complications of such disease, condition or disorder.

Point mutations of the EZH2 gene at a single amino acid residue (e.g., Y641, A677, and A687) of EZH2 have been reported to be linked to lymphoma. More examples of EZH2 mutants and methods of detection of mutation and methods treatment of mutation-associated disorders are described in, e.g., U.S. Patent Application Publication No. US 20130040906, the entire content of which is incorporated herein by reference in its entirety.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3$^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., 18$^{th}$ edition (1990). These texts can, of course, also be referred to in making or using an aspect of the invention.

All percentages and ratios used herein, unless otherwise indicated, are by weight (i.e., weight by weight or wt/wt). Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

EXAMPLES

X-Ray Powder Diffraction
XRPD for all samples was taken on a Rigaku MultiFlex (Target: Cu; Tube voltage: 40 kV; Tube current: 30 mA, at room temperature (about 25° C.), and at 30% relative humidity (RH)).
Differential Scanning Calorimetry
DSC for all samples was taken on a Mettler-Toledo DSC 1/700 (Run conditions: Initial temperature 35° C., Final temp 325-350° C., Heating rate 10-30° C./min).
Dynamic Vapor Sorption
DVS was measured on a VTI Model SGA-100 system. Measurement method: The relative humidity (RH) was changed in a controlled fashion, in 5% steps from 5.0% to 95.0% then back to 5.0% using the gravimetric vapor sorption system, and the weight percentage change (wt %) of the sample at each stage was measured.
Synthesis of Compound I

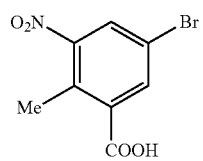 [SMILES: Cc1c(C(=O)O)cc(Br)cc1[N+](=O)[O-]]

5-bromo-2-methyl-3-nitrobenzoic acid

To a stirred solution of 2-methyl-3-nitrobenzoic acid (100 g, 552 mmol) in conc. $H_2SO_4$ (400 mL), 1,3-dibromo-5,5-dimethyl-2,4-imidazolidinedione (88 g, 308 mmol) was added in a portion wise manner at room temperature and the reaction mixture was then stirred at room temperature for 5 h. The reaction mixture was poured onto ice cold water, the precipitated solid was filtered off, washed with water and dried under vacuum to afford the desired compound as a solid (140 g, 98%). The isolated compound was taken directly into the next step. $^1$H NMR (DMSO-$d_6$, 400 MHz) δ 8.31 (s, 1H), 8.17 (s, 1H), 2.43 (s, 3H).

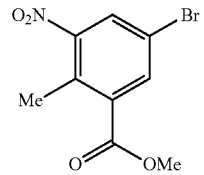 [SMILES: COC(=O)c1cc(Br)cc([N+](=O)[O-])c1C]

Methyl 5-bromo-2-methyl-3-nitrobenzoate

To a stirred solution of 5-bromo-2-methyl-3-nitrobenzoic acid (285 g, 1105 mmol) in DMF (2.8 L) at room temperature was added sodium carbonate (468 g, 4415 mmol) followed by addition of methyl iodide (626.6 g, 4415 mmol). The resulting reaction mixture was heated at 60° C. for 8 h. After completion (monitored by TLC), the reaction mixture was filtered (to remove sodium carbonate) and washed with ethyl acetate (1 L×3). The combined filtrate was washed with water (3 L×5) and the aqueous phase was back extracted with ethyl acetate (1 L×3). The combined organic layers were dried over anhydrous sodium sulfate, filtered and concentrated under reduced pressure to afford the title compound as a solid (290 g, 97% yield). The isolated compound was taken directly into the next step. $^1$H NMR (CDCl$_3$, 400 MHz) δ δ 8.17 (s, 1H), 7.91 (s, 1H), 3.96 (s, 3H), 2.59 (s, 3H).

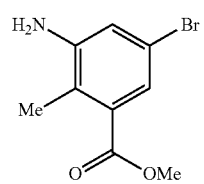 [SMILES: COC(=O)c1cc(Br)cc(N)c1C]

Methyl 3-amino-5-bromo-2-methylbenzoate

To a stirred solution of methyl 5-bromo-2-methyl-3-nitrobenzoate (290 g, 1058 mmol) in ethanol (1.5 L) was added aqueous ammonium chloride (283 g, 5290 mmol dissolved in 1.5 L water). The resulting mixture was stirred at 80° C. to which iron powder (472 g, 8451 mmol) was added in a portion wise manner. The resulting reaction mixture was heated at 80° C. for 12 h. Upon completion as determined by TLC, the reaction mixture was hot filtered over Celite® and the celite bed was washed with methanol (5 L) followed by washing with 30% MeOH in DCM (5 L). The combined filtrate was concentrated in-vacuo, the residue obtained was diluted with aqueous sodium bicarbonate solution (2 L) and extracted with ethyl acetate (5 L×3). The combined organic layers were dried over anhydrous sodium sulfate, filtered and concentrated under reduced pressure to afford the title compound as a solid (220 g, 85%). The compound was taken directly into the next step. $^1$H NMR (CDCl$_3$, 400 MHz) δ 7.37 (s, 1H), 6.92 (s, 1H), 3.94 (s, 3H), 3.80 (bs, 2H), 2.31 (s, 3H).

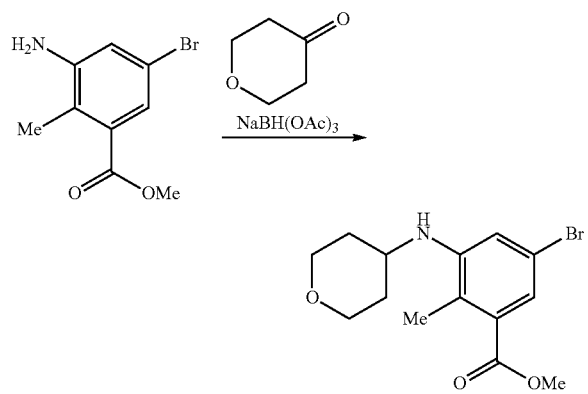

Methyl 5-bromo-2-methyl-3-((tetrahydro-2H-pyran-4-yl) amino) benzoate

A reactor was charged with methyl 3-amino-5-bromo-2-methylbenzoate (455.8 g, 1.87 mol), 1,2-Dichloroethane (4.56 L), and acetic acid (535 ml, 9.34 mol). To the mixture were added dihydro-2H-pyran-4(3H)-one (280 g, 2.80 mol) and sodium triacetoxyborohydride (594 g, 2.80 mol) maintaining the internal temperature below 40° C. The mixture was stirred at 25° C. for 2.5 h and then the reaction was quenched with a solution of sodium hydroxide (448 g, 11.20 mol) in water (5.61 L). After stirring for 20 minutes at ambient temperature, the organic layer was separated and the aqueous layer was extracted with ethyl acetate (3.65 L). The organic layers were combined, washed with brine (1.5 L), and concentrated under vacuum.

The residue was treated with ethyl acetate (1.8 L) and heated to 65-70° C. The mixture was stirred at 65-70° C. for 15 minutes to give a clear solution and then treated with n-heptane (7.3 L) maintaining the temperature between 60-70° C. Once the heptane was completely added to the solution, the mixture was held at 65-70° C. for 15 minutes and then allowed to cool to 18-22° C. over 3 h. The resulting suspension was stirred at 18-22° C. for 4 h, cooled to 0-5° C. over 1 h, and held at 0-5° C. for 2 h. The precipitate was filtered, washed twice with n-heptane (1.4 L), and dried under vacuum to give the title compound (540 g, 88%).

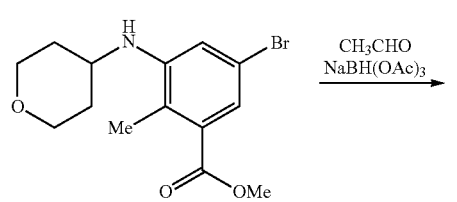

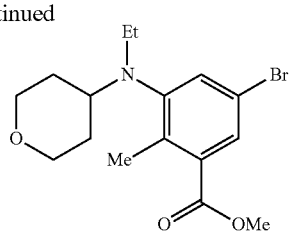

Methyl 5-bromo-3-(ethyl(tetrahydro-2H-pyran-4-yl) amino)-2-methylbenzoate

To a stirred solution of methyl 5-bromo-2-methyl-3-((tetrahydro-2H-pyran-4-yl) amino) benzoate (14 g, 42.7 mmol) in dichloroethane (150 mL) was added acetaldehyde (3.75 g, 85.2 mmol) and acetic acid (15.3 g, 256 mmol). The resulting reaction mixture was stirred at room temperature for 15 minutes. The mixture was cooled to 0° C. and sodium triacetoxyborohydride (27 g, 128 mmol) was added. The reaction mixture was stirred at room temperature for 3 hours. Upon completion of the reaction as determined by TLC, aqueous sodium bicarbonate solution was added to the reaction mixture until a pH 7-8 was obtained, the organic phase was separated and the aqueous phase was extracted with ethyl acetate. The combined organic layers were dried over anhydrous sodium sulfate, filtered and concentrated under reduced pressure. The crude compound was purified by column chromatography (100-200 mesh silica gel) eluting with ethyl acetate:hexane to afford the desired compound as a viscous liquid (14 g, 93%). $^1$H NMR (DMSO-d$_6$, 400 MHz) δ 7.62 (s, 1H), 7.52 (s, 1H), 3.80 (bs, 5H), 3.31 (t, 2H), 2.97-3.05 (m, 2H), 2.87-2.96 (m, 1H), 2.38 (s, 3H), 1.52-1.61 (m, 2H), 1.37-1.50 (m, 2H), 0.87 (t, 3H, J=6.8 Hz).

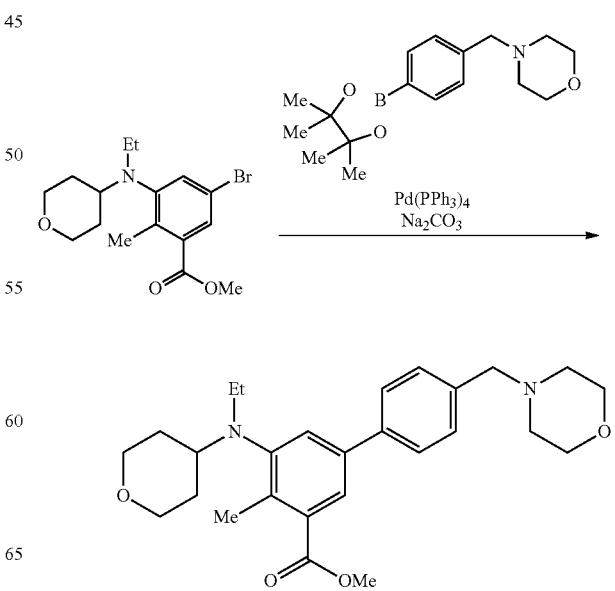

Methyl 5-(ethyl(tetrahydro-2H-pyran-4-yl)amino)-4-methyl-4'-(morpholinomethyl)-[1,1'-biphenyl]-3-carboxylate A mixture of methyl 5-bromo-3-(ethyl(tetrahydro-2H-pyran-4-yl)amino)-2-methylbenzoate (580 g, 1.63 mol), 4-(4-(4,4,5,5-tetramethyl-1,3,2-dioxaborolan-2-yl)benzyl)morpholine (592 g, 1.95 mol), 1,4-dioxane (3.86 L), sodium carbonate (618 g, 5.83 mol), and water (771 ml) was degassed by bubbling nitrogen through the mixture at 20° C. for 20 minutes and treated with tetrakis(triphenylphosphine)palladium(0) (14.11 g, 12.21 mmol). The resulting mixture was degassed for an additional 20 minutes and then heated to 87-89° C. for 17 h. After cooling to 20° C., the mixture was diluted with ethyl acetate (5.80 L) and a solution of (R)-2-Amino-3-mercaptopropionic acid (232 g) in water (2.320 L). After stirring for 1 h at 20° C., the organic layer was separated and washed again with a solution of (R)-2-Amino-3-mercaptopropionic acid (232 g) in water (2.320 L). The aqueous layers were combined and extracted with ethyl acetate (5.80 L). The organic layers were combined, washed with a solution of sodium hydroxide (93 g) in water (2.32 L), and concentrated under vacuum at 35° C. to give the title compound as an orange oil (1.21 kg, 164% yield).

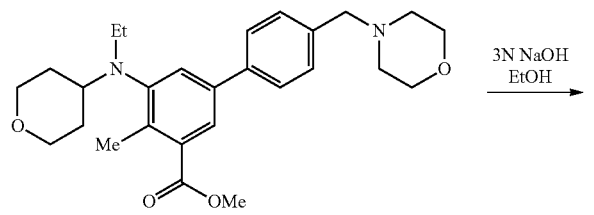

3N NaOH
EtOH
→

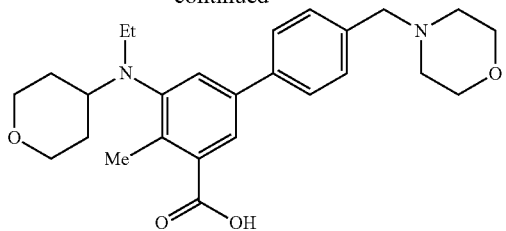

5-(Ethyl(tetrahydro-2H-pyran-4-yl)amino)-4-methyl-4'-(morpholinomethyl)-[1,1'-biphenyl]-3-carboxylic acid Methyl 5-(ethyl(tetrahydro-2H-pyran-4-yl)amino)-4-methyl-4'-(morpholinomethyl)-[1,1'-biphenyl]-3-carboxylate (69.0 g, 152.5 mmol) (based on the theoretical yield from the previous step) was suspended in ethanol (380 mL) and treated with a solution of sodium hydroxide (24.84 g, 621.0 mmol) in water (207 mL). The mixture was stirred at 40° C. for 18 h. After cooling to 0-5° C., the mixture was neutralized to pH 6.5 with 1 N hydrochloric acid (580 mL) maintaining the temperature below 25° C. Then, the mixture was extracted twice with a mixture of dichloromethane (690 mL) and methanol (69.0 mL). The organic layers were combined and concentrated under vacuum to give a crude product as a yellow solid (127 g).

The crude product was dissolved in 2-methyltetrahydrofuran (656 mL) at 70° C. and then treated with IPA (828 mL). The mixture was allowed to cool to rt over 3-4 h and then stirred overnight at rt. The precipitate was filtered, washed twice with IPA (207 mL), and dried under vacuum to give the title compound as an off white solid (53.54 g, 80%).

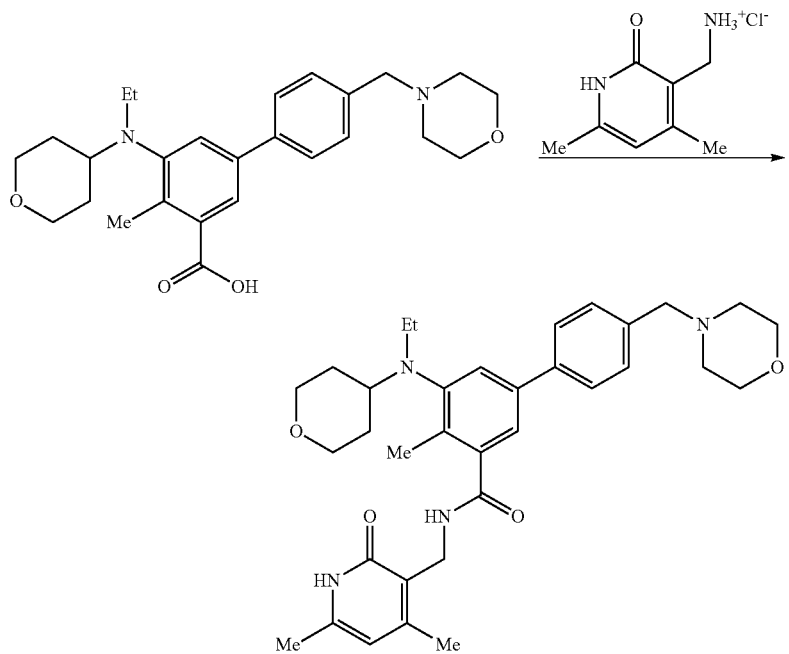

N-((4,6-dimethyl-2-oxo-1,2-dihydropyridin-3-yl)methyl)-5-(ethyhtetrahydro-2H-pyran-4-yl)amino)-4-methyl-4'-(morpholinomethyl)-[1,1'-biphenyl]-3-carboxamide (Compound I)

A mixture of 5-(ethyl(tetrahydro-2H-pyran-4-yl)amino)-4-methyl-4'-(morpholinomethyl)-[1,1'-biphenyl]-3-carboxylic acid (540 g, 1.23 mol) and 3-(aminomethyl)-4,6-dimethyl-dihydro-pyridin-2(1H)-one hydrochloride (279 g, 1.48 mol) was suspended in DMSO (2.70 L) and treated with triethylamine (223 ml, 1.60 mol). The mixture was stirred at 25° C. for 30 min and treated with EDC-HCl (354 g, 1.85 mol) and HOBT hydrate (283 g, 1.85 mol). The reaction mixture was stirred at rt for 16 h. After addition of triethylamine (292 ml, 2.09 mol), the mixture was cooled to 15° C., diluted with water (10.1 L) maintaining the temperature below 30° C., and stirred at 19-25° C. for 4 h. The resulting precipitate was filtered, washed twice with water (2.70 L), and dried under vacuum to give a crude product (695 g, wt-wt analysis=78%).

For the further purification of the product, recrystallization was conducted. A crude product (20.00 g, 34.92 mmol) was suspended in a mixture of ethanol (190 ml) and water (10.00 ml) and heated to 75° C. until a clear solution was obtained. The solution was allowed to cool to rt overnight. The precipitate was filtered, washed twice with a mixture of ethanol (30.0 ml) and water (30.0 ml), and dried under vacuum at 35° C. to give the title compound as an off white solid (14.0 g, 70% recovery from the crude and 90% yield based on wt-wt assay).

Preparation of Polymorph C 4-((3'-(((4,6-Dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)methyl)morpholin-4-ium chloride

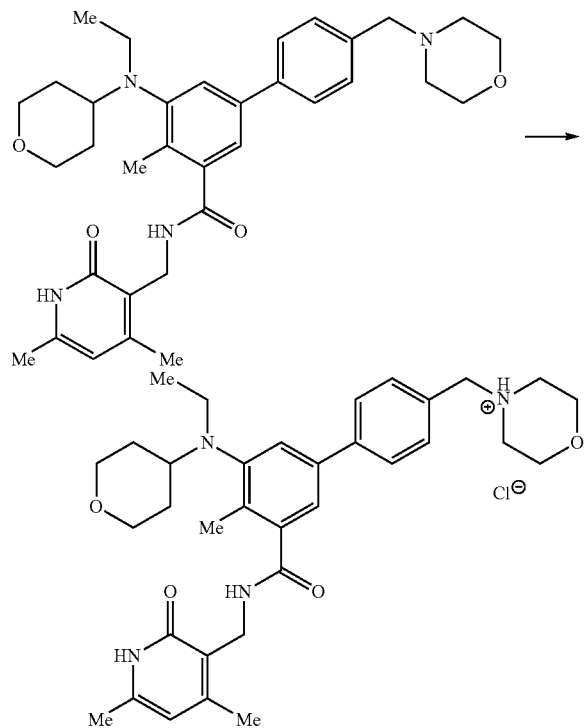

A suspension of N-((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide (10.0 g, 17.46 mmol) in ethanol (70.0 ml) was heated to 70° C. (bath) and treated with conc HCl (1.455 ml, 17.46 mmol). The mixture was stirred at 70° C. for 20 min and then treated with ethyl acetate (140.0 ml). The resulting mixture was stirred at 70° C. for 30 min and slowly cooled to room temperature over 20 h. The resulting precipitate was filtered, washed with ethyl acetate (20 mL) and dried over $N_2$ purge for 20 h to give Polymorph C (6.17 g, 63%).

Preparation of Polymorph A 4-((3'-(((4,6-Dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)methyl)morpholin-4-ium chloride (Polymorph A)

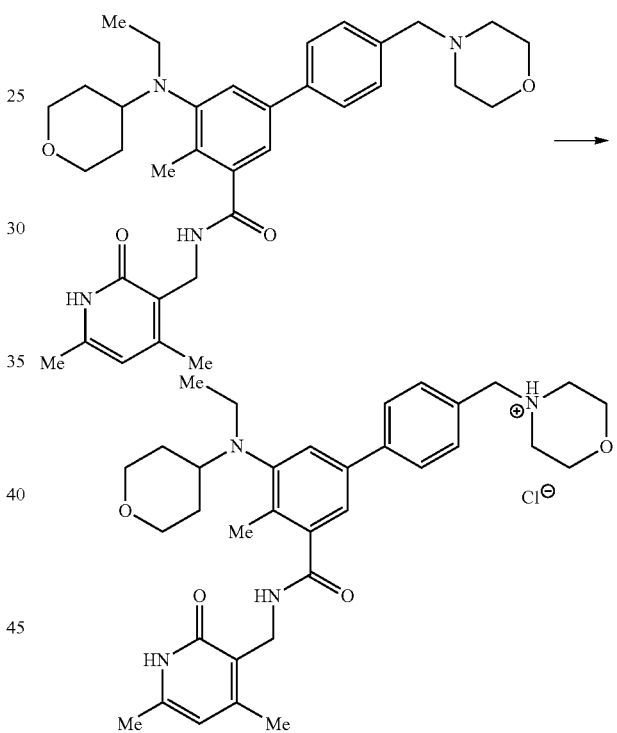

A suspension of N-((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide (100 mg, 0.18 mmol) in a mixture of ethanol (0.2 mL) and water (0.1 mL) was heated to 80° C. (bath) and treated with conc. HCl (0.29 mL, 3.49 mmol). The resulting clear solution was treated with ethanol (1 ml) at 80° C. (bath), and stirred at 40° C. (bath) for 30 min and at rt for 16 h. The resulting precipitate was filtered, washed with ethanol (1 mL) and dried over $N_2$ purge to give a crude title compound (60 mg).

The crude HCl salt was treated with ethyl acetate (1 mL), heated to 80° C. (bath), and treated with methanol (0.15 mL) to give a clear solution. The mixture was stirred at ambient temperature for 16 h. The precipitate was filtered, washed with ethyl acetate, and dried over $N_2$ purge to give the title compound of Polymorph A (54 mg, 51%).

Preparation of Polymorph B 4-((3'-(((4,6-Dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)methyl)morpholin-4-ium chloride (Polymorph B)

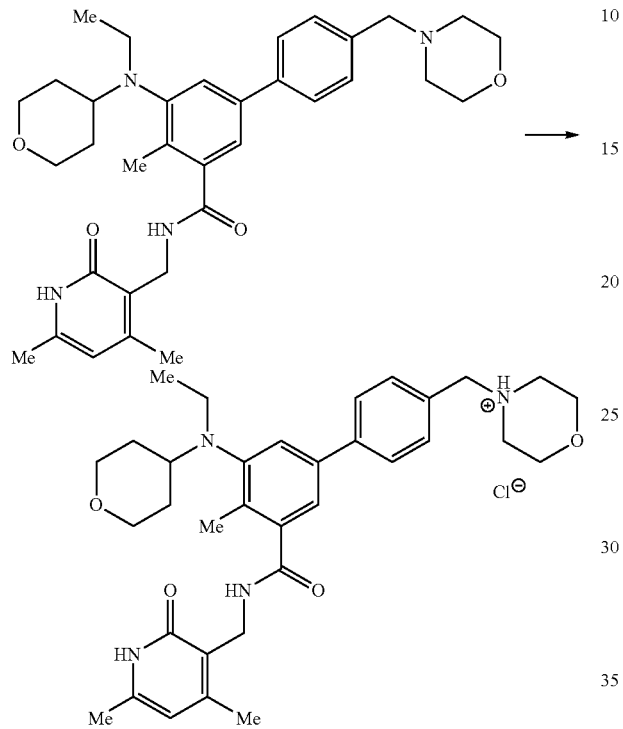

N-((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide (2.0 g, 3.49 mmol) was suspended in a mixture of methanol (2.65 mL) and ethyl acetate (2.65 mL), and heated to 60° C. (bath). The mixture was treated with conc. HCl (0.29 mL, 3.49 mmol). The resulting clear dark solution was treated with ethyl acetate (10 ml), stirred at 60° C. (bath) for 10 min, and slowly cooled to rt over 20 h. The resulting precipitate was filtered, washed twice with ethyl acetate (5 mL) and dried over $N_2$ purge for 4 h to give a crude title compound (2.05 g, 96%).

Polymorph B was prepared by two methods:
a) 200 mg of the crude HCl salt was treated with acetonitrile (3 mL), heated to 70° C. (bath), and treated with water (0.3 mL) to give a clear solution. The mixture was stirred at 70° C. (bath) for 10 min and slowly cooled to rt over 20 h. The precipitate was filtered, washed with acetonitrile, and dried under vacuum for 4 h to give the title compound of Polymorph B (160 mg, 80%).
b) 200 mg of the crude HCl salt was treated with acetone (3 mL), heated to 70° C. (bath), and treated with water (0.45 mL) to give a clear solution. The mixture was stirred at 70° C. (bath) for 10 min and slowly cooled to rt over 20 h. The precipitate was filtered, washed with acetonitrile, and dried under vacuum for 4 h to give the title compound of Polymorph B (152 mg, 76%).

Tables

TABLE 1

| Polymorph A 2-Theta |
|---|
| 11.22 |
| 12.0 |
| 13.116 |
| 13.418 |
| 13.899 |
| 17.026 |
| 18.032 |
| 18.32 |
| 19.399 |
| 20.199 |
| 21.84 |
| 22.499 |
| 23.238 |
| 24.363 |
| 24.7 |
| 24.958 |
| 30.557 |
| 30.879 |

TABLE 2

| Polymorph B 2-Theta |
|---|
| 8.438 |
| 10.18 |
| 10.74 |
| 13.318 |
| 13.541 |
| 13.762 |
| 16.443 |
| 17.219 |
| 17.78 |
| 18.419 |
| 20.182 |
| 20.421 |
| 20.839 |
| 21.958 |
| 23.725 |
| 24.159 |
| 25.498 |
| 26.863 |

TABLE 3

| Polymorph C 2-Theta |
|---|
| 10.083 |
| 10.940 |
| 16.583 |
| 17.124 |
| 17.534 |
| 18.340 |
| 18.662 |
| 20.500 |
| 21.143 |
| 21.917 |
| 22.219 |
| 23.460 |
| 26.222 |
| 26.596 |
| 27.722 |
| 30.299 |

TABLE 4

| Polymorph | Polymorph A | Polymorph B | Polymorph C |
|---|---|---|---|
| Onset temperature (° C.) | 190 ± 5° C. | 105 ± 5° C. | 228 ± 5° C. (primary endotherm) |

Characteristics of Polymorph Forms

Three solid crystalline forms of Compound I hydrochloride were prepared and characterized. These forms are identified herein as Polymorph A, Polymorph B and Polymorph C. Among them, Polymorph C had the most advantageous physicochemical properties in terms of stability (cf. FIG. 4) and hygroscopicity (cf. FIGS. 5 and 6). The formation of Polymorph C as described herein is also advantageous in that it results in a form of Compound I HCl that is substantially free of amorphous Compound I (or its amorphous mono- or multi-HCl forms).

Figure 6:
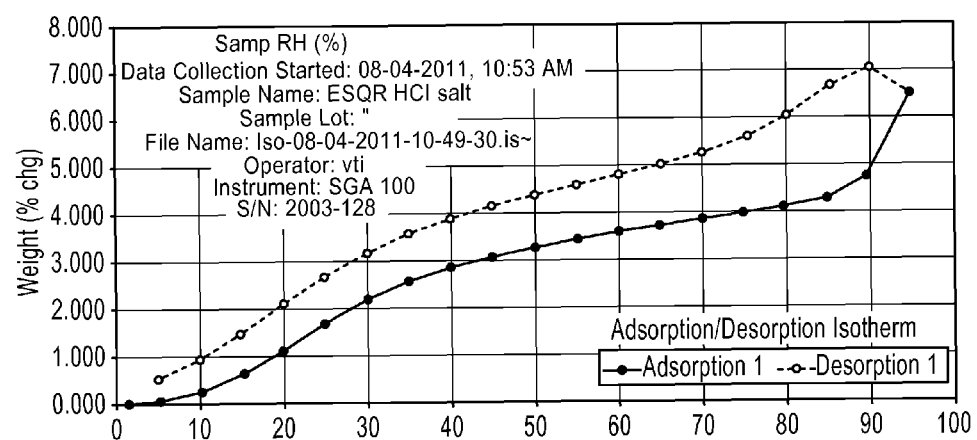
FIG. 6 depicts DVS data for Polymorph A.
Figure 7:
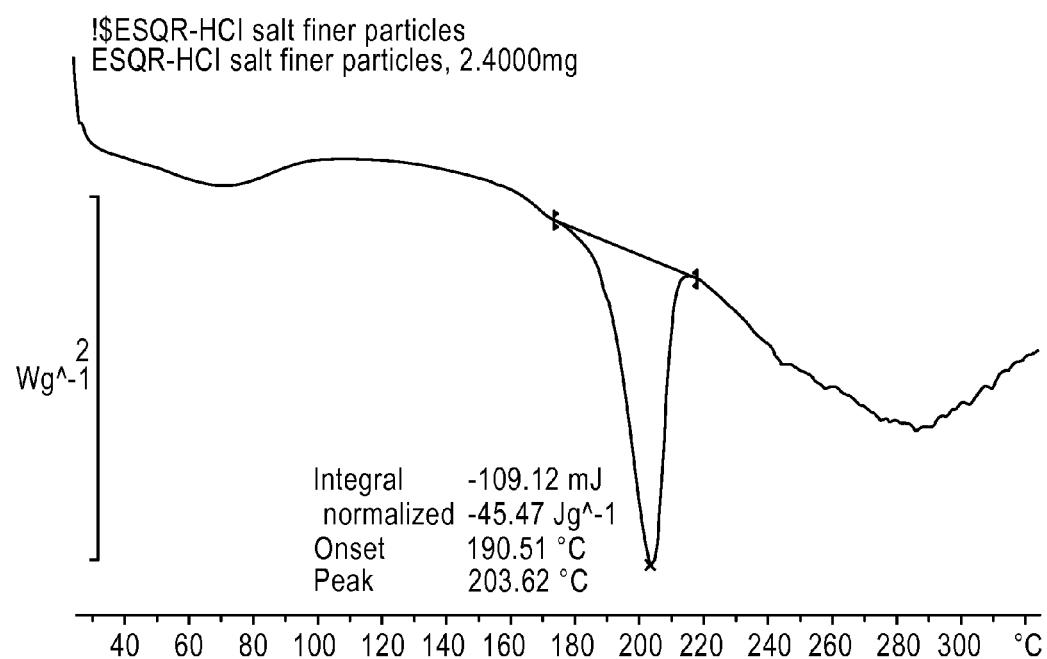
FIG. 7 depicts DSC data for Polymorph A.

As shown in FIG. 7, DSC data of Polymorph A indicates some degree of non-crystallinity with an endotherm at 190.5° C. Also, dynamic vapor sorption (DVS) data for Polymorph A was obtained and found to show some hygroscopicity: between 4-6% weight gain was observed at 75% relative humidity (RH) at 25° C. (FIG. 6).

Surprisingly, Polymorph C was found to be highly crystalline and stable (with the highest endotherm of the three polymorphic forms discussed herein; see FIG. 4) and non-hygroscopic (FIG. 5).

The entire disclosure of each of the patent documents and scientific articles referred to herein is incorporated by reference for all purposes.

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

The invention claimed is:

1. A solid crystalline form of N-((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide, or a salt thereof, wherein the solid crystalline form exhibits an X-ray powder diffraction pattern having two or more peaks expressed in degrees 2-theta (+/−0.2), selected from the group consisting of 8.438, 10.083, 10.18, 10.74, 10.940, 11.22, 12.0, 13.116, 13.318, 13.418, 13.541, 13.762, 13.899, 16.443, 16.583, 17.026, 17.124, 17.219, 17.53, 17.78, 18.032, 18.32, 18.340, 18.419, 18.66, 19.399, 20.182, 20.199, 20.421, 20.500, 20.839, 21.14, 21.84, 21.917, 21.958, 22.22, 22.499, 23.238, 23.46, 23.725, 24.159, 24.363, 24.7, 24.958, 25.498, 26.222, 26.596, 26.863, 27.72, 30.30, 30.557, and 30.879.

2. The solid crystalline form of claim 1, wherein the solid crystalline form exhibits an X-ray powder diffraction pattern having two or more characteristic peaks expressed in degrees 2-theta (+/−0.2), selected from the group consisting of 17.53, 18.66, 21.14, 22.22, 23.46, 27.72 and 30.30.

3. The solid crystalline form of claim 1, wherein the solid crystalline form exhibits an X-ray powder diffraction pattern having three or more characteristic peaks expressed in degrees 2-theta (+/−0.2), selected from the group consisting of 17.53, 18.66, 21.14, 22.22, 23.46, 27.72 and 30.30.

4. The solid crystalline form of claim 1, wherein the solid crystalline form exhibits an X-ray powder diffraction pattern having characteristic peaks expressed in degrees 2-theta (+/−0.2) at 17.53, 21.14, 23.46, and 27.72.

5. The solid crystalline form of claim 1, wherein the solid crystalline form exhibits a differential scanning calorimetry thermogram showing a primary endotherm expressed in units of ° C. at a temperature of 190+/−5° C., 105+/−5° C. or 228+/−5° C.

6. A pharmaceutical composition comprising a polymorph of claim 1, and a pharmaceutically acceptable carrier or diluent.

7. The solid crystalline form of claim 1, wherein the solid crystalline form exhibits an X-ray powder diffraction pattern having two or more characteristic peaks expressed in degrees 2-theta (+/−0.2), selected from the group consisting of 11.22, 12.0, 13.116, 18.032, 19.399, 22.499, 24.363, 24.7, 24.958, 30.557, and 30.879.

8. The solid crystalline form of claim 1, wherein the solid crystalline form exhibits an X-ray powder diffraction pattern having three or more characteristic peaks expressed in degrees 2-theta (+/−0.2), selected from the group consisting of 11.22, 12.0, 13.116, 18.032, 19.399, 22.499, 24.363, 24.7, 24.958, 30.557, and 30.879.

9. The solid crystalline form of claim 1, wherein the solid crystalline form exhibits an X-ray powder diffraction pattern having two or more characteristic peaks expressed in degrees 2-theta (+/−0.2), selected from the group consisting of 8.438, 13.318, 17.78, 23.725, 24.159, 25.498 and 26.863.

10. The solid crystalline form of claim 1, wherein the solid crystalline form exhibits an X-ray powder diffraction pattern having three or more characteristic peaks expressed in degrees 2-theta (+/−0.2), selected from the group consisting of 8.438, 13.318, 17.78, 23.725, 24.159, 25.498 and 26.863.

11. The solid crystalline form of claim 1, wherein the solid crystalline form exhibits an X-ray powder diffraction pattern having two or more peaks expressed in degrees 2-theta (+/−0.2) selected from the group consisting of about 10.083, 10.940, 13.418, 13.899, 16.583, 17.124, 17.53, 18.340, 18.66, 20.199, 20.500, 20.839, 21.917, and 23.46.

12. The solid crystalline form of claim 1, wherein the solid crystalline form exhibits an X-ray powder diffraction pattern having two or more peaks expressed in degrees 2-theta (+/−0.2) selected from the group consisting of 10.940, 13.418, 13.899, 16.583, 17.124, 18.340, and 20.199.

13. The solid crystalline form of claim 1, wherein the solid crystalline form exhibits an X-ray powder diffraction pattern having peaks expressed in degrees 2-theta (+/−0.2) at 17.124, 18.340, and 21.917.

14. A solid crystalline form of N-((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide monohydrochloride, wherein the solid crystalline form exhibits an X-ray powder diffraction pattern having two or more peaks expressed in degrees 2-theta (+/−0.2), selected from the group consisting of 17.124, 18.340 and 21.917.

* * * * *